(12) United States Patent
Nicolo

(10) Patent No.: US 6,592,600 B1
(45) Date of Patent: Jul. 15, 2003

(54) BOWEL CLAMP

(76) Inventor: Enrico Nicolo, 1515 Timberlane, Clairton, PA (US) 15025

( * ) Notice: Subject to any disclaimer, the term of this patent is extended or adjusted under 35 U.S.C. 154(b) by 320 days.

(21) Appl. No.: 09/168,649

(22) Filed: Oct. 8, 1998

Related U.S. Application Data
(60) Provisional application No. 60/061,455, filed on Oct. 8, 1997.

(51) Int. Cl.$^7$ ............................................. A61B 17/08
(52) U.S. Cl. ...................................... 606/157; 606/207
(58) Field of Search ................................. 606/151, 139, 606/205–208

(56) References Cited

U.S. PATENT DOCUMENTS

| | | | | |
|---|---|---|---|---|
| 943,263 A | * | 12/1909 | Moraweck | 606/205 |
| 1,472,380 A | * | 10/1923 | Atwood | 606/151 |
| 4,950,275 A | * | 8/1990 | Donini | 606/151 |
| 5,241,968 A | * | 9/1993 | Slater | 606/205 |
| 5,366,459 A | * | 11/1994 | Yoon | 606/151 |
| 5,368,596 A | * | 11/1994 | Burkhart | 606/151 |
| 5,713,919 A | * | 2/1998 | Lahr | 606/207 |

OTHER PUBLICATIONS

Advertisement entitled "Cuschieri Prehensile Grasper" (2 pp.) appearing in Storz Karl Storz–Endoskope catalog (Feb. 1998).

* cited by examiner

Primary Examiner—Gary Jackson
(74) Attorney, Agent, or Firm—Webb Ziesenheim Logsdon Orkin & Hanson, P.C.

(57) ABSTRACT

A surgical clamp allows for mobilization of an organ or hollow viscus of a patient during a surgical procedure with minimization of trauma to the organ or hollow viscus. The surgical clamp includes at least one handle adapted to be gripped by the user for manipulation of the surgical clamp and the engaged organ or hollow viscus, and at least on jaw attached to the handle, wherein the jaw is adapted to substantially encircle the engaged organ or hollow viscus of the patient. The clamp may be sized to fit through a conventional trocar such that the surgical procedure may be a laparoscopic procedure for operating on the organ or hollow viscus, such as the bowel.

20 Claims, 4 Drawing Sheets

BOWEL CLAMP

This application claims the benefit of U.S. Provisional Patent Application Ser. No. 60/061,455, filed on Oct. 8, 1997, entitled "Bowel Clamp", which is incorporated herein by reference.

BACKGROUND OF THE INVENTION

1. Field of the Invention

My invention relates to surgical clamps for organ manipulation, more particularly my invention relates to non-traumatic laparoscopic bowel clamps which encircle the bowel.

2. Background Information

During many surgical procedures it is necessary to mobilize and move the bowel. This is particularly true during resection of the bowel. During open surgical procedures, the surgeon can accomplish the movement of the bowel manually without significant risk of damaging the bowel. However, during laparoscopic surgical procedures, manual movement of the bowel is no longer possible. In order to achieve movement of the bowel during laparoscopic procedures, various bowel engaging clamps have been developed. One such clamp is known as the Babcock clamp, which fits through the trocar and grips directly onto the bowel. The surgeon will utilize the clamp for moving the bowel appropriately during operative procedures.

The existing bowel clamps are designed to clamp directly on the bowel. The direct clamping or pinching engagement with the bowel wall results in a significant number of drawbacks. The engagement of the clamp on the bowel can puncture the bowel wall. Additionally, the movement of the bowel by using the engaged clamp can tear the bowel. This is due, in part, to the minimal surface engagement between the clamp and the bowel wall.

When the bowel wall is compromised, whether by the bowel engaging clamp or otherwise, numerous complications can arise. First, the contamination of the interior body cavity with the dirty contents of the bowel interior can increase the risk of infection and other adverse affects. Furthermore, once a puncture or tear has occurred, the surgeon has to take appropriate remedial measures. These remedial measures may include further resection of the bowel to include the bowel segment which has been damaged, or separately stitching or otherwise closing the puncture or tear in the bowel to repair the damage caused by the clamp. Either of these remedial measures increases the time of the surgery. Additionally, both of these remedial measures increase the risk of infection and the like to the patient by exposing the contents in the interior of the bowel to the interior of the body cavity. Therefore, this damage to the bowel needs to be avoided.

It is an object of the present invention to overcome the drawbacks of the prior art. It is a further object of the present invention to provide a bowel clamp which can be easily used in laparoscopic or open procedures for engaging and moving the bowel while significantly reducing the risk of damaging the bowel.

SUMMARY OF THE INVENTION

The above objects are achieved by a bowel clamp according to my invention. A bowel clamp according to my invention is designed to not clamp directly onto the bowel, but instead is designed to substantially encircle the bowel. In operation, the bowel clamp of my invention can be inserted through a small opening in the mesentery of the bowel so that when the bowel clamp is closed, the bowel will rest completely inside the jaw face of the bowel clamp. The bowel clamp of my invention evenly distributes the forces associated with movement or mobilization of the bowel across the bowel wall to minimize damage of the bowel wall. In this manner when the bowel is moved by the bowel clamp in any direction, the bowel will not be damaged, perforated or torn.

The bowel clamp of my invention may be designed to compress or slightly crimp the bowel while encircling the bowel in order to better reinforce the bowel wall to further minimize potential damage and increase mobility of the bowel while using the bowel clamp of the present invention.

The bowel clamp of my invention may include a jaw formed of a first jaw member pivotally connected to a second jaw member at a pivot point at one end of the jaw members. Each jaw member may includes a jaw tip at a distal end thereof. The jaw tips are adapted to abut against each other when the jaw members are in a closed position. When the jaw members are in the closed position, the jaw members combine to define a bowel encircling opening between the jaw members, the pivot and the tips.

In one embodiment, the bowel clamp includes cross-pivoted handles attached to each jaw member on opposite sides of the pivot. Additionally, one jaw member may form a cradle for receiving the bowel prior to closing. The bowel clamp of the present invention is preferably closable to 10–12 mm for easy use in laparoscopic procedures.

In another embodiment of my invention, the entire jaw of the bowel clamp is pivotable about a pivot point. The entire jaw may also be rotatable about the jaw pivot point. The articulation and rotation of the entire jaw provides the mobility needed for manipulating the clamped bowel. Preferably the articulation and rotation of the jaw as well as the closing of the individual jaw members can be controlled remotely through a trocar.

In one embodiment of my invention the jaw of the bowel clamp is a flexible member, such as a tube or strap, extending from the handle. The handle may also include a clasping member to secure the flexible member to the handle after the flexible member has formed a loop around the bowel.

These and other advantages of the present invention will be clarified in the Description of the Preferred Embodiments taken together with the attached figures wherein like reference numerals represent like elements throughout.

DESCRIPTION OF THE PREFERRED EMBODIMENTS

Figure 1:
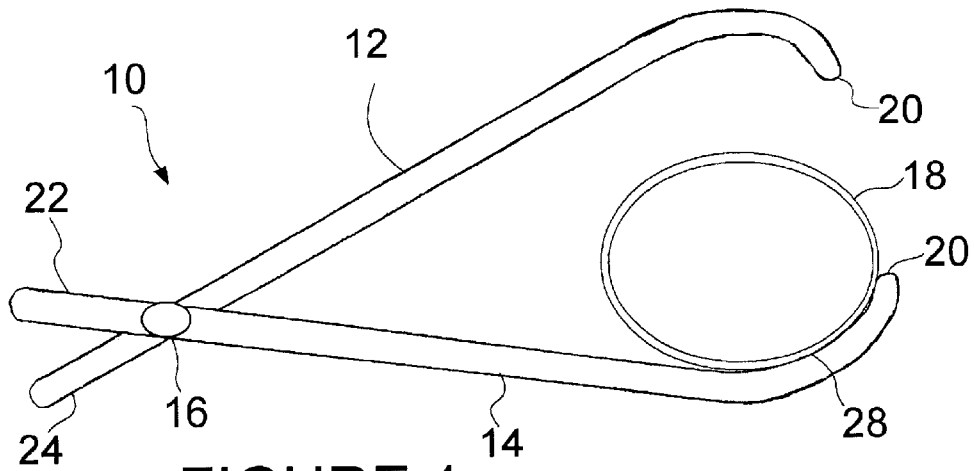
FIG. 1 is a side view schematically illustrating a bowel clamp according to my invention.
Figure 3:
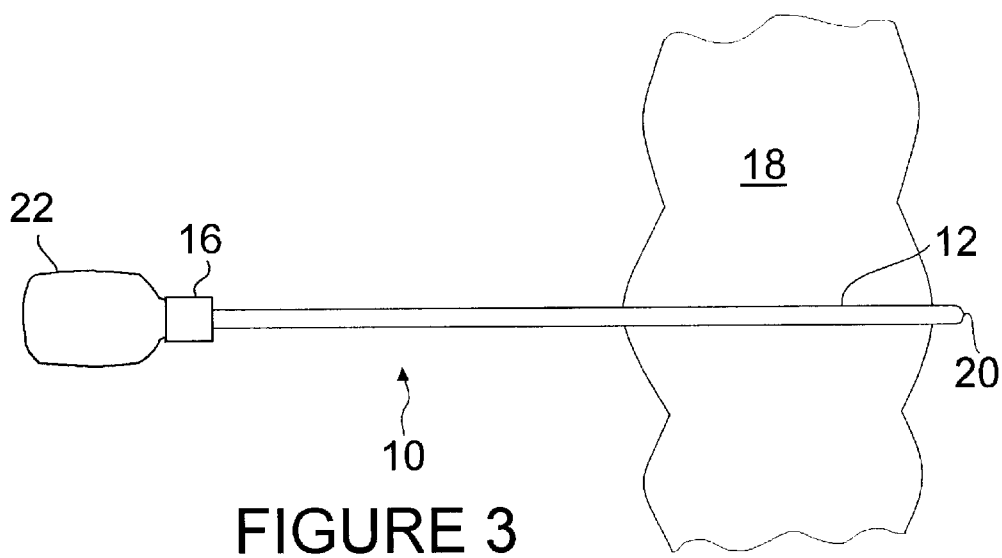
FIG. 3 is a top view of the bowel clamp illustrated in FIG. 2.
Figure 2:
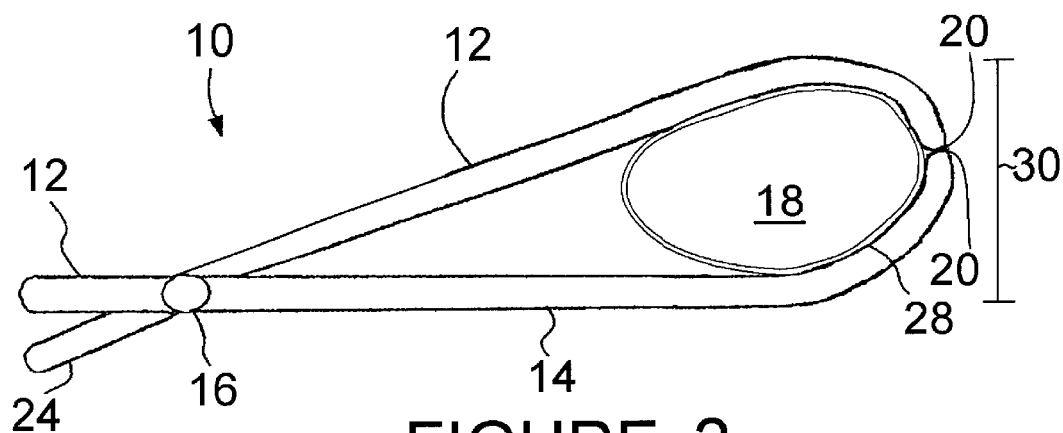
FIG. 2 is a side view of the bowel clamp in the first position according to my invention.

FIGS. 1–3 illustrate a bowel clamp 10 according to a first embodiment of my invention. As shown in FIG. 2, the bowel clamp 10 includes a jaw 11 formed of jaw members 12 and 14 pivotally attached together at one end thereof by pivot 16. Each jaw member 12 and 14 preferably extends far enough from the pivot 16 to traverse the bowel 18 as shown in FIGS. 1–3. At the distal end of each jaw member 12 and 14 is a blunted tip 20. The tips 20 are adapted to abut against each other when the bowel clamp 10 is moved in the closed position as illustrated in FIG. 2. The forming of the tips 20 as rounded, relatively flat members minimizes the risk of puncturing the bowel 18 during the clamping operation if the jaw members 12 and 14 have not been positioned properly to extend completely across the bowel 18. The blunted tips 20 may be formed of any size and of alternative shapes. The tips 20 may be formed with interengaging recesses and projections to provide a secure jaw 11 in the clamped position for movement of the bowel. Additionally, the tips 20 may be provided with an adjustment mechanism, such as a set screw extending toward the other tip 20, to adjust the clamped distance between the jaw members 12 and 14. The bowel clamp 10 includes attached handles 22 and 24 (shown for illustrative purposes only) attached to the jaw members 14 and 12, respectively, for opening and closing of the jaw members 12 and 14. The handles 22 and 24 may be replaced with more conventional handle members which can extend through a trocar for remote operation of the jaw members 12 and 14.

The jaw members 12 and 14, the tips 20 and the handles 22 and 24 may be formed of any conventional material such as metal or plastic.

The jaw 11 of the bowel clamp 10 includes a bowel encircling opening 26 formed by the jaw members 12 and 14, between the jaw members 12 and 14, pivot 16 and the engaged tips 20 as shown in FIGS. 1 and 2. Each of the jaw members 12 and 14 preferably have rounded edges to avoid surfaces which could damage the wall of the bowel 18. The jaw members 12 and 14 may also be coated with a softer material (i.e. rubber, foam element, plastic) which further reduces stress on the engaged bowel. The widths of the jaw members 12 and 14 should be relatively substantial in order to increase the surface contact area between the bowel 18 and the bowel clamp 10 to further distribute the stresses between the bowel clamp 10 and the bowel 18. This will further minimize the risk of damage to the bowel 18. The face of each jaw member engaging with the bowel may be smooth or may be grooved to be less traumatic to the engaged portion of the bowel.

As shown in FIG. 1, the lower jaw member 14 is asymmetrical to the upper jaw member 12 forming a general J-shape providing a cradle 28 for receiving and positioning the bowel 18 during the clamping operation. The height 30 of the bowel clamp 10 is preferably sized appropriately to allow for fitting the bowel clamp 10 through an associated trocar for use in laparoscopic procedures. For example, the height 30 of the bowel clamp 10 may be 10–12 mm allowing the bowel clamp 10 to fit through an associated 12 mm trocar. Separately sized clamps 10 will be associated with conventionally sized trocars, such as 12 mm, 11 mm, 10 mm, 5 mm, 3 mm, and 2 mm. Additionally, the clamps 10 may be sized for the intended use. For example, difficult sizes would be associated with pediatric applications or a dilated bowel. The construction of the clamps 10 of these dimensions will include the construction of jaw members 12 and 14 with a length and height which accommodates conventional bowels. The smaller sizes may require a jaw 11 construction which expands after it has passed through the associated trocar. Appropriate expansion may be accomplished through the use of an elastically deformable material, such as spring steel, or a shape memory alloy which recovers an expanded shape.

The bowel clamp 10 of my invention operates as follows. Bowel clamp 10 is designed to encircle the bowel 18 through a small opening in the mesentery of the bowel 18. The bowel 18 will be positioned in the cradle 28 of the lower jaw member 14 prior to moving of the upper jaw 12 to the closed position. The positioning of the bowel 18 in the cradle 28 is preferably observed directly by the surgeon prior to closing of the bowel clamp 10. With the bowel 18 in the cradle 28, the bowel clamp 10 is moved to the closed position so that the tips 20 are abutting against each other and the bowel clamp 10 completely encircles the bowel 18. The bowel 18 may be slightly crimped and is held in the bowel encircling opening 26 within the jaw of the bowel clamp 10. The bowel clamp 10 of my invention may slightly crimp the bowel 18 to further reduce the risk of damage to the bowel 18. The bowel clamp 10 of my invention does not clamp directly onto the bowel 18 as in prior art. As discussed above, the bowel clamp 10 of my invention is designed to encircle the bowel 18 and to slightly crimp the bowel 18. These features of my invention provide a bowel clamp 10 resulting in greater mobility of the bowel 18 with significantly reduced damage to the bowel 18. The encircling of the bowel 18 eliminates the risk of puncturing the bowel 18 during the clamping procedure. Additionally, the encircling of the bowel increases the surface contact area between the clamp 10 and the bowel 18 better distributing the forces during movement of the bowel 18 by the bowel clamp 10. Furthermore, the clamping of the bowel 18 within the jaw 11 adds further support to the bowel 18 to further reduce the risk of damage. With the bowel clamp 10 in the operative position, the bowel 18 can be easily moved in any direction as needed by the surgeon.

Figure 4:
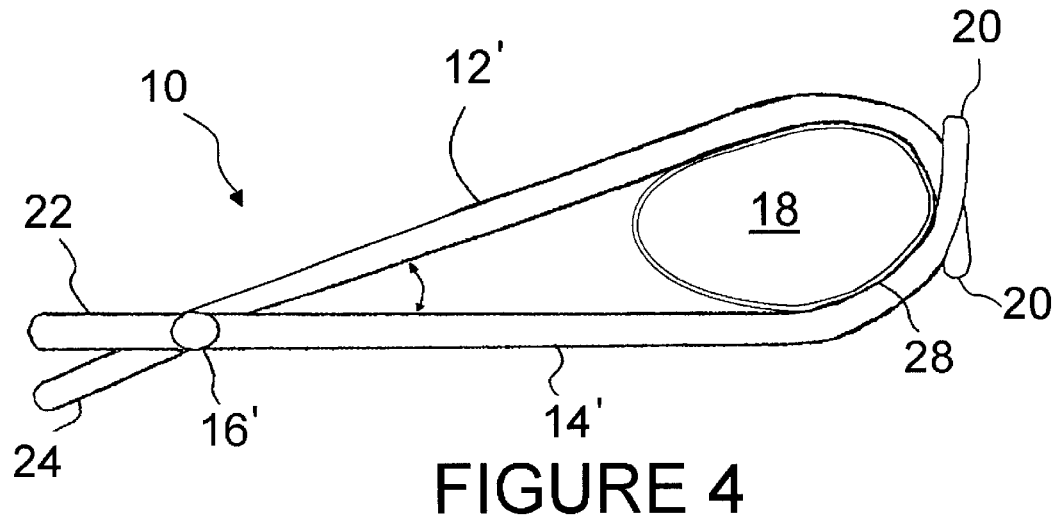
FIG. 4 is a side view of an alternative embodiment of the bowel clamp according to my invention.

Many modifications may be made to the bowel clamp of my invention. FIG. 4 illustrates a modification which allows the bowel clamp 40, illustrated therein, to provide a jaw 11 of greater height. The bowel clamp 40, illustrated in FIG. 4, includes all the features of the bowel clamp 10, illustrated in FIG. 1, except that jaw members 12' and 14' are illustrated as substantially identical. Additionally, the pivot 16' of the bowel clamp 40 together with the construction of the jaw members 12' and 14' allows the respective jaw members 12' and 14' to be moved out of plane and in overlapping arrangement as illustrated in FIG. 4. The overlapping arrangement allows the bowel clamp 40 to be easily moved through an associate trocar. After being moved through the trocar, the jaw members 12' and 14' are moved back into the same plane so that the respective tips 20 can engage to completely encircle the bowel 18 in the same manner as discussed above in connection with bowel clamp 10. The overlapping of the jaw members 12' and 14' may be provided by forming the jaw members 12' and 14' from elastic material (e.g. spring steel, plastic, or the like).

Figure 5:
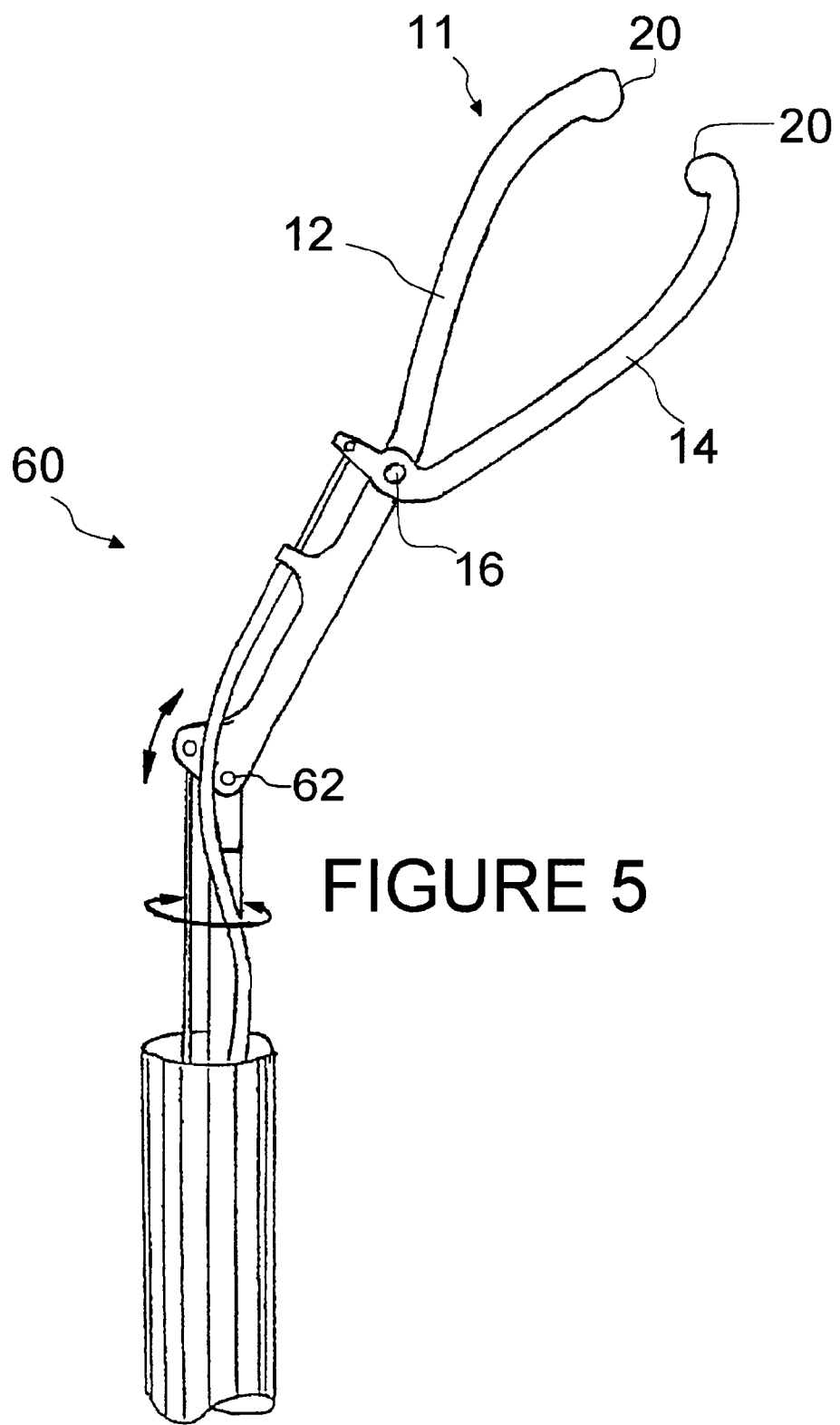
FIG. 5 is a schematic side view of an alternative embodiment of the bowel clamp according to my invention.

FIG. 5 is a schematic side view of an alternative embodiment of a bowel clamp 60 according to my invention. The bowel clamp 60, illustrated in FIG. 5, includes all the features of the bowel clamp 10, illustrated in FIG. 1. The jaw actuating components for the bowel clamp 60 differs from the simpler construction of the cross-pivotal handles shown in FIGS. 1–4. Bowel clamp 60 includes a flexible actuating cable attached to jaw member 14 for actuating the jaw 11. Additionally, the entire jaw 11 of the bowel clamp 60 is pivotable about a pivot point 62 spaced behind pivot point 16. The entire jaw 11 is also rotatable as shown by the arrow in FIG. 5. The articulation and rotation of the entire jaw 11 provides the mobility needed for manipulating the clamped bowel. Preferably the articulation and rotation of the jaw 11 as well as the closing of the individual jaw members 12 and 14 can be controlled remotely through a trocar using known types of controls.

Figure 6A:
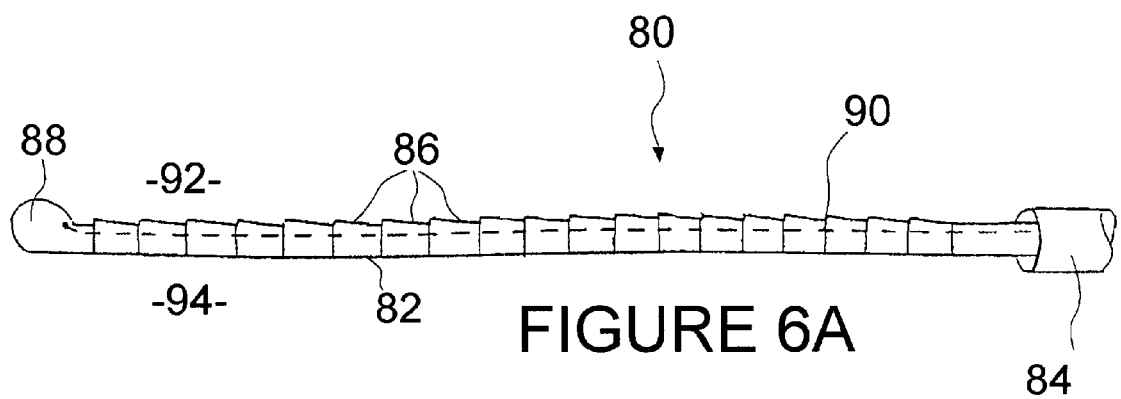
FIGS. 6*a* and 6*b* are schematic side views of an alternative embodiment of the bowel clamp according my invention.
Figure 6B:
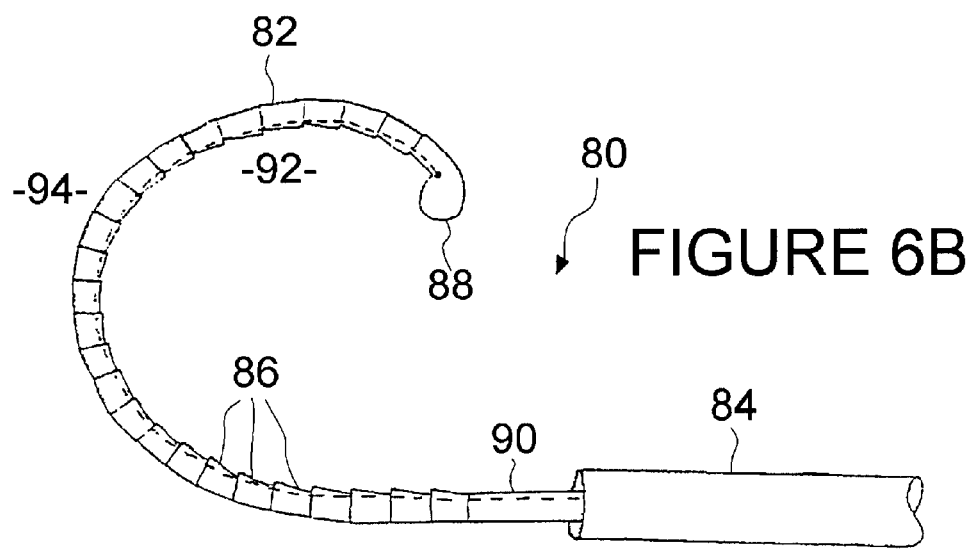

FIGS. 6a and 6b are schematic side views of an alternative embodiment of a bowel clamp 80 according my invention. The bowel clamp 80 forms the jaw 11 from a flexible member 82 extending from a handle 84. The flexible member 82 includes a plurality of segments 86 and a tip 88. A cord 90 is arranged inside the segments 86 and an end of the cord 90 is attached to the tip 88 of the flexible member. By pulling on the cord 90, the segments 86 will slide into each other on one side 92 of the segments 86 and the segments will stay in abutting contact with each other on the other side 94 of the segments 86. Essentially, the segments 86 are pivotably connected to each other on one side 94 thereof. Because of this, the flexible member 82 will curl around, for example, the bowel, as shown in FIG. 6b.

The flexible member 82 may also be an inflatable tube incorporating a spring which biases or curls the flexible member 82 toward the operative position. The flexible member 82 may be straightened by inflating the tube with, for example, compressed air. The handle 84 may include a clasp (not shown) which can secure the flexible member 82 to the handle 84 after the flexible member 82 has formed a loop around the bowel 18 as shown in FIG. 6B. Clamp 80 is illustrative of the breadth of my invention. Many variations of the clamp according to my invention are possible. The main object of my invention is to provide a bowel clamp which substantially completely encircles the bowel and does not clamp directly onto the bowel.

It would be apparent to those of ordinary skill in the art that further modifications may be made to my invention without departing from the spirit and scope thereof. My present invention is primarily a bowel clamp which encircles the bowel for increased mobility of the bowel during operation with decreased risk of puncture, tearing or other damage to the bowel. However, the clamp of my invention may be used on other organs to avoid puncturing, tearing or other damage to the organ. For example, the clamp of my invention may be designed to encircle the appendix for manipulation and removal of the appendix during an appendectomy. The clamps may be designed and sized for other organs or any hollow viscus, such as the esophagus, blood vessels or ureter. The organ claim of my invention encircles the organ rather than clamping directly onto the organ.

The above-described examples are merely illustrative of my present invention and not restrictive thereof. Consequently, the scope of my invention is defined by the appended claims and equivalents thereto.

I claim:

1. A surgical clamp for engaging and mobilizing an organ or hollow viscus of a patient, said clamp comprising:

at least one handle adapted to be gripped by the user for manipulation of said clamp and the engaged organ or hollow viscus; and a pair of pivoted jaws are coupled to said at least one handle, wherein said pair of jaws are adapted to completely encircle the engaged organ or hollow viscus, and wherein said pair of jaws are pivotable relative to said at least one handle about at least a second pivot point.

2. The surgical clamp of claim 1 wherein said clamp is sized to fit through a conventional trocar.

3. A surgical clamp for engaging and mobilizing an organ or hollow viscus of a patient, said clamp comprising:

at least one handle adapted to be gripped by the user for manipulation of said clamp and the engaged organ or hollow viscus; and at least one jaw coupled to said at least one handle, wherein said at least one jaw is adapted to substantially encircle the engaged organ or hollow viscus, wherein a maximum height of said clamp is less than about 12 mm and wherein said clamp is sized to fit through a conventional trocar.

4. The surgical clamp of claim 3 wherein a pair of pivoted jaws are provided, said pair of jaws adapted to completely encircle the engaged organ or hollow viscus.

5. The surgical clamp of claim 2 wherein said pair of pivoted jaws are substantially identical in shape.

6. The surgical clamp of claim 2 wherein said pair of jaws are asymmetrical in shape, wherein one of said pair of jaws forms a J-shape defining a cradle for receiving the organ or hollow viscus.

7. The surgical clamp of claim 2 wherein tips of said pivoted jaws are adapted to abut each other to encircle the organ or hollow viscus, and wherein said tips are rounded members.

8. The surgical clamp of claim 2 wherein said pair of jaws are pivotable relative to said at least one handle about at least a second pivot point.

9. A surgical clamp for engaging and mobilizing an organ or hollow viscus of a patient, said clamp comprising:

at least one handle adapted to be gripped by the user for manipulation of said clamp and the engaged organ or hollow viscus; and at least one jaw coupled to said at least one handle, wherein said at least one jaw is adapted to substantially encircle the engaged organ or hollow viscus, wherein said at least one jaw includes a flexible member moveable between at least a substantially straight non-engaging position and a curved engaging position adapted to substantially encircle the organ or hollow viscus.

10. A surgical bowel clamp for engaging and mobilizing a bowel of a patient during surgery, said bowel clamp comprising:

at least one handle adapted to be gripped by the user for manipulation of said clamp and the engaged bowel; and at least on jaw coupled to said at least one handle, wherein said at least one jaw is adapted to substantially encircle the bowel, wherein said clamp is sized to fit through a conventional trocar.

11. The bowel clamp of claim 10 wherein a pair of pivoted jaws are provided, said pair of jaws adapted to completely encircle the bowel.

12. The bowel clamp of claim 11 wherein said pair of jaws are asymmetrical in shape, wherein one of said pair of jaws includes a cradle for receiving the bowel.

13. The bowel clamp of claim 11 wherein tips of said pivoted jaws are adapted to abut each other to encircle the bowel.

14. The bowel clamp of claim 11 wherein said pair of pivoted jaws are substantially identical in shape.

15. The bowel clamp of claim 10 wherein a maximum height of said clamp is less than about 12 mm.

16. The bowel clamp of claim 11 wherein said pair of jaws are pivotable relative to said at least one handle about at least a second pivot point.

17. The bowel clamp of claim 10 wherein said at least one jaw includes a flexible member moveable between at least a substantially straight non-engaging position and a curved engaging position adapted to substantially encircle the organ or hollow viscus.

18. The bowel clamp of claim 17 wherein said flexible member includes a plurality of pivotably connected segments.

19. A method of mobilizing an organ or hollow viscus of a patient during a surgical procedure comprising the steps of:

provided a surgical clamp including at least one handle adapted to be gripped by the user for manipulation of said clamp and the engaged organ or hollow viscus, and at least on jaw attached to said at least one handle, wherein said at least one jaw is adapted to substantially encircle the engaged organ or hollow viscus;

encircling the organ or hollow viscus with said jaws of said clamp; and manipulating the organ or hollow viscus by gripping said handle and moving said clamp.

20. The method of claim 19 wherein said organ or hollow viscus is the bowel of the patient and wherein said surgical procedure is a laparoscopic surgical procedure.

* * * * *